United States Patent [19]
Araneo

[11] Patent Number: 5,929,060
[45] Date of Patent: Jul. 27, 1999

[54] METHOD FOR ENHANCING OR ACCELERATING RE-EPITHELIALIZATION OR RE-ENDOTHELIALIZATION OF A TISSUE

[75] Inventor: Barbara A. Araneo, Salt Lake City, Utah

[73] Assignee: University of Utah Research Foundation, Salt Lake City, Utah

[21] Appl. No.: 08/695,769

[22] Filed: Aug. 1, 1996

Related U.S. Application Data

[63] Continuation-in-part of application No. 08/480,748, Jun. 7, 1995, Pat. No. 5,686,438, and application No. 08/483,524, Jun. 7, 1995, abandoned, said application No. 08/480,748, is a continuation-in-part of application No. 08/284,688, Aug. 9, 1994, Pat. No. 5,532,230, which is a continuation-in-part of application No. 08/029,442, Mar. 9, 1993, abandoned, said application No. 08/483,524, is a continuation-in-part of application No. 08/152,002, Nov. 10, 1993, abandoned, which is a continuation-in-part of application No. 07/877,612, May 1, 1992, abandoned.

[51] Int. Cl.$^6$ .................................................... A61K 31/56
[52] U.S. Cl. ............................................................ 514/178
[58] Field of Search ............................................... 514/178

[56] References Cited

U.S. PATENT DOCUMENTS 5,489,581   2/1996   Daynes et al. ........................... 514/178

*Primary Examiner*—Joseph Conrad
*Attorney, Agent, or Firm*—Rothwell, Figg, Ernst & Kurz, P.C.

[57] ABSTRACT

The present invention is related to a method for enhancing or accelerating re-epithelialization or re-endothelialization of a tissue. Examples of re-epithelialization in which the invention is particularly suited include, but are not limited to, re-epithelialization of (a) skin following surgical wounds, (b) skin abrasions caused by mechanical trauma, caustic agents or burns, (c) cornea following cataract surgery or corneal transplants, (d) mucosal epithelium (respiratory, gastrointestinal, genitourinary, mammary, oral cavity, ocular tissue, liver and kidney) following infection, nonpathological etiologies or drug therapy, (e) skin following grafting and (f) renal tubule following acute tubular necrosis. Examples of re-endothelialization in which the invention is particularly suited include, but are not limited to, re-endothelialization (or regrowth of endothelium) in blood vessels following angioplasty, and the lysis of fibrin clots or lysis or mechanical disruption of thrombi in coronary arteries. In accordance with the present invention, the time to complete re-epithelialization or re-endothelialization is enhanced or accelerated by administering a dehydroepiandrosterone (DHEA) derivative.

19 Claims, 3 Drawing Sheets

METHOD FOR ENHANCING OR ACCELERATING RE-EPITHELIALIZATION OR RE-ENDOTHELIALIZATION OF A TISSUE

CROSS-REFERENCE TO RELATED APPLICATIONS

The present application is a continuation-in-part of application Ser. No. 08/480,748 now U.S. Pat. No. 5,686,438, filed Jun. 7, 1995, and of application Ser. No. 08/483,524, filed Jun. 7, 1995 now abandoned. Ser. No. 08/480,748 is in turn a continuation-in-part of Ser. No. 08/284,688, filed Aug. 9, 1994 now U.S. Pat. No. 5,532,230, which in turn is a continuation-in-part of Ser. No. 08/029,442 filed Mar. 9, 1993 now abandoned. Ser. No. 08/483,524 in turn is a continuation-in-part of application Ser. No. 08/152,002, filed Nov. 10, 1993 now abandoned, which is a continuation-in-part of Ser. No. 07/877,612, filed May 1, 1992 now abandoned. Each of these applications is incorporated herein by reference.

BACKGROUND OF THE INVENTION

The present invention is related to a method for enhancing or accelerating re-epithelialization or re-endothelialization of a tissue. Examples of re-epithelialization in which the invention is particularly suited include, but are not limited to, re-epithelialization of (a) skin following surgical wounds, (b) skin abrasions caused by mechanical trauma, caustic agents or burns, (c) cornea following cataract surgery or corneal transplants, (d) mucosal epithelium (respiratory, gastrointestinal, genitourinary, mammary, oral cavity, ocular tissue, liver and kidney) following infection, nonpathological etiologies or drug therapy, (e) skin following grafting and (f) renal tubule following acute tubular necrosis. Examples of re-endothelialization in which the invention is particularly suited include, but are not limited to, re-endothelialization (or regrowth of endothelium) in blood vessels following angioplasty, lysis of fibrin clots or lysis or mechanical disruption of thrombi in coronary arteries. The invention is especially suited for the re-epithelialization of donor sites from which epidermal tissue is harvested for application to burn sites and for repair of the tissue and microvasculature of thermally injured skin. In accordance with the present invention, the time to complete re-epithelialization or re-endothelialization is enhanced or accelerated by administering a dehydroepiandrosterone (DHEA) derivative.

The publications and other materials used herein to illuminate the background of the invention and in particular cases, to provide additional details respecting the practice, are incorporated by reference, and for convenience are numerically referenced in the following text and respectively grouped in the appended bibliography.

After a lesion occurs in the epidermis, it becomes critical to survival that access of the environment to the dermis is blocked without delay. In this event, the body effects wound closure in two temporally related steps: within minutes by the formation of a blood clot, which reestablishes a temporary barrier, and then within hours to days by the movement of residual epithelium below the clot and over the underlying dermis—the process of re-epithelialization. The first step, involving blood clot formation and its dependence on vessel wall, platelets and coagulation proteins, is the subject of a recent review (1).

Characteristic of all epithelial cells is the propensity to cover a free surface. Clearly, in order to cover a denuded surface, epithelial cells must (1) move, and (2) grow over that wounded area. Although both processes are stimulated by wounding, the more important process in early wound closure is cell migration, which is independent of cell division (2–6). Indeed, under experimental conditions, blocking of cell division has no effect on the rate of epithelial cell movement or wound closure (7–9). The migrating cells arise from the residual epithelium at the periphery of the lesion or, more often, from the residual hair or sweat structure at the wound base. In large, deep cutaneous lesions, the epithelium that covers the wound area arises from the wound periphery. In small, superficial cutaneous wounds, however, most of the epithelium arises from the residual pilosebaceous or eccrine structure (5, 10, 11). Recent observations suggest, however, that under some circumstances mesenchymal cells may transform and become part of the regenerating epithelium (12); however, that phenomenon probably plays a minor role in the closure of most wounds.

Re-epithelialization occurs most rapidly over a superficial wound that leaves the basement membrane zone intact. In the repair of a suction blister, for example, in which the floor of the wound consists of an intact lamina densa (suction causes the separation of the epidermis from the dermis within the lamina lucida), short tongues of epithelial cells rapidly (within 12 to 24 hours) grow out from the residual epithelial structures (13). By 24 to 72 hours, most of the wound base is covered by a thin layer of epithelium, and by four days it is covered by layered keratinocytes (13, 14).

In all systems, it is the basal cell, i.e., the cell attached to the substratum, that responds to wounding and initiates migration. These marginal cells flatten out in the direction of the wound and send out cytoplasmic projections over the substratum (15, 16). In preparation for their movement, the epithelial cells loosen their intercellular and substratum attachments. They have hemidesmosomal junctions, their tonofilaments withdraw from the cell periphery, and the basement membrane zone becomes less well-defined (13, 17–19). In addition, the cells at the leading edge become actively phagocytic, picking up tissue debris and erythrocytes. This phagocytic property of epidermal cells can be illustrated in the laboratory, using fluorescein-coated beads or Thorotrast particles, which are taken up by epidermal cells (16, 17, 20). This property is enhanced by the fibronectin in wound fluid (21).

Within one or two days, epithelial cells behind the migrating front begin to proliferate, generating new populations of cells to cover the wound (6, 13). Once epithelialization is complete and the wound area is covered, the epithelial cells revert to their normal prototype and reassume their intercellular and basement membrane contacts.

Re-epithelialization over any wound will occur, like an unrolling carpet or a military phalanx, by the movement of epithelial cells as a sheet. Considering the tight intercellular cohesions that epithelial cells share, it is not surprising that these cells do not migrate over a wound as single cells, but instead as small clusters or sheets. When sheets of epithelial cells have been observed directly, the cells at the margin of the moving sheet appeared to be actively motile while the cells behind (or above, in a stratified layer) the marginal cells were passively dragged along (22, 23). If attachment of the marginal cells to the substrate is disturbed, the migrating sheet, under tension, will withdraw. This mode of sheet movement, referred to as the sliding model of wound closure, has been demonstrated directly for epithelial cells in tissue culture (22), for embryonic epithelial movement (24), for amphibian wound closure (23), and for corneal wound closure (25).

It is much more difficult to study mammalian cutaneous wound closure directly because of the thickness and opacity of the dermis. Moreover, the migrating epithelial sheet of mammalian epidermis is multi-layered and thus more complex than those systems illustrating the sliding model. For the repairing mammalian epidermis, Winter (26) proposed the "leap-frog" model or epidermal sheet movement. This model was deduced indirectly from ultrastructural morphological data which suggested that cells at the migrating front adhere to the substrate only to be replaced at the front, in turn, by the cells above and behind it. Successively, then, submarginal cells are conceived to crawl over the newly adherent basal cells in a leap-frog fashion. Cell marker studies have been presented in support of this model wherein keratin antigens found in suprabasal cells of the intact epidermis (K10, K1) are found in the basal cells of the migrating tip. Although one may ascribe these results to cell movement, these changes may also be explained by the ability of keratinocytes to switch their differentiation pattern after injury to express a keratin that normally is not found among the cells in the basal layer (28). Although the data are indirect, the leap-frog model of mammalian epidermal wound closure has many proponents (6, 13, 27–30). As the issue is not yet resolved, it is currently reasonable to contend that simple epithelium moves by the sliding model while multilayered epithelium may manifest a more complex pattern. In mammals, either or both mechanisms (sliding and leap-frogging) may function in wound closure, depending on the state and character of the epithelium affected (31).

It is desired to identify compounds which will enhance the rate of or accelerate re-epithelialization or re-endothelialization, thus aiding in the re-epithelialization or re-endothelialization of tissue such as noted above.

DHEA is an endogenous androgenic steroid which serves as the primary precursor in the biosynthesis of both androgens and estrogens (32) and which has been shown to have a myriad of biological activities. DHEA has been reported to play a mitigating role in obesity, diabetes, carcinogenesis, autoimmunity, neurological loss of memory (33–36), and the negative effects of GCS on IL-2 production by murine T cells (37). Araneo et al. (38) has shown that the administration of DHEA to burned mice within one hour after injury resulted in the preservation of normal immunologic competence, including the normal capacity to produce T-cell-derived lymphokines, the generation of cellular immune responses and the ability to resist an induced infection. Eich et al. (39, 40) describes the use of DHEA to reduce the rate of platelet aggregation and the use of DHEA or DHEA-sulfate (DHEA-S) to reduce the production of thromboxane, respectively.

Nestler et al. (41) shows that administration of DHEA was able in human patients to reduce body fat mass, increase muscle mass, lower LDL cholesterol levels without affecting HDL cholesterol levels, lower serum apolipoprotein B levels, and not affect tissue sensitivity to insulin. Kent (42) reported DHEA to be a "miracle drug" which may prevent obesity, aging, diabetes mellitus and heart disease. DHEA was widely prescribed as a drug treatment for many years. However, the Food and Drug Administration recently restricted its use. DHEA is readily interconvertible with its sulfate ester DHEA-S through the action of intracellular sulfatases and sulfotransferases.

Daynes et al. (43) shows that administration of certain DHEA derivatives are useful for the reducing or preventing progressive tissue necrosis, reperfusion injury, bacterial translocation and and adult respiratory distress syndrome. Daynes et al. (44) shows that the administration of DHEAS and other DHEA derivatives are also suitable for these uses. Finally, Araneo et al. (45) shows that DHEA derivatives are useful for reducing or preventing pulmonary hypertension. Despite the myriad of biological activities reported for DHEA derivatives, DHEA derivatives have not been reported to have any affect on re-epithelialization.

SUMMARY OF THE INVENTION

The present invention is related to a method for enhancing or accelerating re-epithelialization or re-endothelialization of a tissue. Examples of re-epithelialization in which the invention is particularly suited include, but are not limited to, re-epithelialization of (a) skin following surgical wounds, (b) skin abrasions caused by mechanical trauma, caustic agents or burns, (c) cornea following cataract surgery or corneal transplants, (d) mucosal epithelium (respiratory, gastrointestinal, genitourinary, mammary, oral cavity, ocular tissue, liver and kidney) following infection, nonpathological etiologies or drug therapy, (e) skin following grafting and (f) renal tubule following acute tubular necrosis. Examples of re-endothelialization in which the invention is particularly suited include, but are not limited to, re-endothelialization (or regrowth of endothelium) in blood vessels following angioplasty, lysis of fibrin clots or lysis or mechanical disruption of thrombi in coronary arteries. In accordance with the present invention, the rate of re-epithelialization or re-endothelialization is enhanced or accelerated by administering a dehydroepiandrosterone (DHEA) derivative.

BRIEF DESCRIPTION OF THE FIGURES

FIG. 1 shows the results for mature adult mice (▲), aged mice (■) and aged mice with DHEAS treatment (●).

FIG. 2 shows the results for the control (vehicle, ■), 4 mg/kg dose of DHEAS (●) and 12 mg/kg dose of DHEAS (▲).

DETAILED DESCRIPTION OF THE INVENTION

Figure 1:
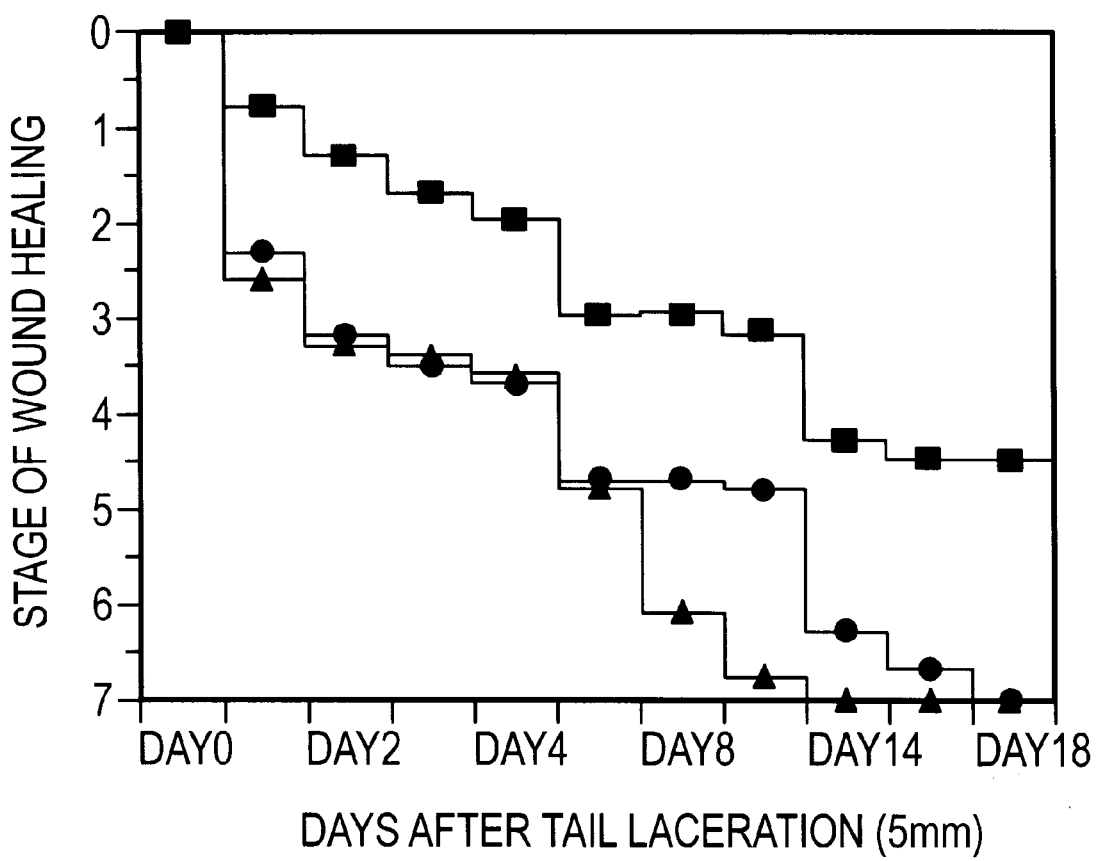
FIG. 1 shows the effect of DHEAS on wound healing in mice.

The present invention is related to a method for enhancing or accelerating re-epithelialization or re-endothelialization of a tissue. Examples of re-epithelialization in which the invention is particularly suited include, but are not limited to, re-epithelialization of (a) skin following surgical wounds, (b) skin abrasions caused by mechanical trauma, caustic agents or burns, (c) cornea following cataract surgery or corneal transplants, (d) mucosal epithelium (respiratory, gastrointestinal, genitourinary, mammary, oral cavity, ocular tissue, liver and kidney) following infection, nonpathological etiologies or drug therapy, (e) skin following grafting and (f) renal tubule following acute tubular necrosis. Examples of re-endothelialization in which the invention is particularly suited include, but are not limited to, re-endothelialization (or regrowth of endothelium) in blood vessels following angioplasty, and the lysis of fibrin clots or lysis or mechanical disruption of thrombi in coronary arteries. In accordance with the present invention, the time to complete re-epithelialization or re-endothelialization is enhanced or accelerated administering a dehydroepiandrosterone (DHEA) derivative, preferably intravenously, to a patient in need of re-epithelialization or re-endothelialization.

Examples of a DHEA derivative, include but are not limited to, compounds having the formula

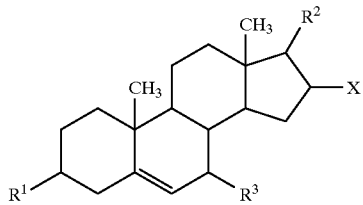

wherein

X is H or halogen;

$R^1$, $R^2$ and $R^3$ are independently =O, —OH, —SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —$OSO_2R^5$ or —$OPOR^5R^6$;

$R^5$ and $R^6$ are independently —OH, pharmaceutically acceptable esters or pharmaceutically acceptable ethers; and pharmaceutically acceptable salts.

Thus, examples of suitable DHEA congeners include compounds in which:

(1) $R^2$ is =O, $R^3$ and X are each H and $R^1$ is =O, —OH, pharmaceutically acceptable esters thereof, pharmaceutically acceptable ethers thereof or pharmaceutically acceptable salts;

(2) $R^2$ is =O, $R^3$ is H, X is halogen and $R^1$ is =O, —OH, pharmaceutically acceptable esters thereof, pharmaceutically acceptable ethers thereof or pharmaceutically acceptable salts;

(3) $R^2$ is =O, $R^3$ and X are each H and $R^1$ is —SH, pharmaceutically acceptable thioesters thereof, pharmaceutically acceptable thioethers thereof or pharmaceutically acceptable salts;

(4) $R^2$ is =O, $R^3$ is H, X is halogen and $R^1$ is —SH, pharmaceutically acceptable thioesters thereof, pharmaceutically acceptable thioethers thereof or pharmaceutically acceptable salts;

(5) $R^2$ is =O, X is H and $R^1$ and $R^3$ are independently =O, —OH, pharmaceutically acceptable esters thereof, pharmaceutically acceptable ethers thereof or pharmaceutically acceptable salts;

(6) $R^2$ is =O, X is halogen and $R^1$ and $R^3$ are independently =O, —OH, pharmaceutically acceptable esters thereof, pharmaceutically acceptable ethers thereof or pharmaceutically acceptable salts;

(7) $R^2$ is =O, X is H and $R^1$ and $R^3$ are independently —SH, pharmaceutically acceptable thioesters thereof, pharmaceutically acceptable thioethers thereof or pharmaceutically acceptable salts;

(8) $R^2$ is =O, X is halogen and $R^1$ and $R^3$ are independently —SH, pharmaceutically acceptable thioesters thereof, pharmaceutically acceptable thioethers thereof or pharmaceutically acceptable salts;

(9) $R^2$ is —OH, $R^3$ and X are each H and $R^1$ is =O, —OH, pharmaceutically acceptable esters thereof, pharmaceutically acceptable ethers thereof or pharmaceutically acceptable salts;

(10) $R^2$ is —OH, $R^3$ is H, X is halogen and $R^1$ is =O, —OH, pharmaceutically acceptable esters thereof, pharmaceutically acceptable ethers thereof or pharmaceutically acceptable salts;

(11) $R^2$ is —OH, $R^3$ and X are each H and $R^1$ is —SH, pharmaceutically acceptable thioesters thereof, pharmaceutically acceptable thioethers thereof or pharmaceutically acceptable salts;

(12) $R^2$ is —OH, $R^3$ is H, X is halogen and $R^1$ is —SH, pharmaceutically acceptable thioesters thereof, pharmaceutically acceptable thioethers thereof or pharmaceutically acceptable salts;

(13) $R^2$ is —OH, X is H and $R^1$ and $R^3$ are independently =O, —OH, pharmaceutically acceptable esters thereof, pharmaceutically acceptable ethers thereof or pharmaceutically acceptable salts;

(14) $R^2$ is —OH, X is halogen and $R^1$ and $R^3$ are independently =O, —OH, pharmaceutically acceptable esters thereof, pharmaceutically acceptable ethers thereof or pharmaceutically acceptable salts;

(15) $R^2$ is —OH, X is H and $R^1$ and $R^3$ are independently —SH, pharmaceutically acceptable thioesters thereof, pharmaceutically acceptable thioethers thereof or pharmaceutically acceptable salts;

(16) $R^2$ is —OH, X is halogen and $R^1$ and $R^3$ are independently —SH, pharmaceutically acceptable thioesters thereof, pharmaceutically acceptable thioethers thereof or pharmaceutically acceptable salts;

(17) $R^2$ is —SH, $R^3$ and X are each H and $R^1$ is =O, —OH, pharmaceutically acceptable esters thereof, pharmaceutically acceptable ethers thereof or pharmaceutically acceptable salts;

(18) $R^2$ is —SH, $R^3$ is H, X is halogen and $R^1$ is =O, —OH, pharmaceutically acceptable esters thereof, pharmaceutically acceptable ethers thereof or pharmaceutically acceptable salts;

(19) $R^2$ is —SH, $R^3$ and X are each H and $R^1$ is —SH, pharmaceutically acceptable thioesters thereof, pharmaceutically acceptable thioethers thereof or pharmaceutically acceptable salts;

(20) $R^2$ is —SH, $R^3$ is H, X is halogen and $R^1$ is —SH, pharmaceutically acceptable thioesters thereof, pharmaceutically acceptable thioethers thereof or pharmaceutically acceptable salts;

(21) $R^2$ is —SH, X is H and $R^1$ and $R^3$ are independently =O, —OH, pharmaceutically acceptable esters thereof, pharmaceutically acceptable ethers thereof or pharmaceutically acceptable salts;

(22) $R^2$ is —SH, X is halogen and $R^1$ and $R^3$ are independently =O, —OH, pharmaceutically acceptable esters thereof, pharmaceutically acceptable ethers thereof or pharmaceutically acceptable salts;

(23) $R^2$ is —SH, X is H and $R^1$ and $R^3$ are independently —SH, pharmaceutically acceptable thioesters thereof, pharmaceutically acceptable thioethers thereof or pharmaceutically acceptable salts;

(24) $R^2$ is —SH, X is halogen and $R^1$ and $R^3$ are independently —SH, pharmaceutically acceptable thioesters thereof, pharmaceutically acceptable thioethers thereof or pharmaceutically acceptable salts;

(25) X is H and $R^1$, $R^2$ and $R^3$ are independently =O, —OH, a sugar residue, pharmaceutically acceptable esters thereof, pharmaceutically acceptable ethers thereof or pharmaceutically acceptable salts, wherein at least one of $R^1$, $R^2$ and $R^3$ is a sugar residue;

(26) X is halogen and $R^1$, $R^2$ and $R^3$ are independently =O, —OH, a sugar residue, pharmaceutically acceptable esters thereof, pharmaceutically acceptable ethers thereof or pharmaceutically acceptable salts, wherein at least one of $R^1$, $R^2$ and $R^3$ is a sugar residue;

(27) X is H and $R^1$, $R^2$ and $R^3$ are independently =O, —OH, pharmaceutically acceptable inorganic esters thereof or pharmaceutically acceptable salts, wherein at least one of $R^1$, $R^2$ and $R^3$ is an inorganic ester;

(28) X is halogen and $R^1$, $R^2$ and $R^3$ are independently =O, —OH, pharmaceutically acceptable inorganic esters thereof or pharmaceutically acceptable salts, wherein at least one of $R^1$, $R^2$ and $R^3$ is an inorganic ester.

Pharmaceutically acceptable esters or thioesters include, but are not limited to, esters or thioesters of the formula —OOCR or —SOCR, wherein R is a pharmaceutically acceptable alkyl, alkenyl, aryl, alkylaryl, arylalkyl, sphingosine or substituted sphingolipid groups, such as propionate, enanthate, cypionate, succinate, decanoate and phenylpropionate esters.

Pharmaceutically acceptable ethers or thioethers include, but are not limited to, ethers or thioethers of the formula —OR or —SR, wherein R is as defined above or enol, or —$OR^4$ is an unsubstituted or substituted spirooxirane or —SR is a spirothiane.

Suitable sugar residues include, but are not limited to monosaccharides, disaccharides and oligosaccharides, such as a glucuronate.

Pharmaceutically acceptable inorganic esters include, but are not limited to, inorganic esters of the formula —$OSO_2R^5$ or —$OPOR^5R^6$, wherein $R^5$ and $R^6$ are independently —OH, pharmaceutically acceptable esters, pharmaceutically acceptable ethers or pharmaceutically acceptable salts.

Initial investigations demonstrated that the administration of DHEA or DHEAS restored T-cell responsiveness to platelet derived growth factor (PDGF). It is known that PDGF and various other growth factors are involved in wound healing, angiogenesis and other repair processes. In studies detailed below, it was discovered that administration of DHEAS to aged mice enhanced the rate of wound closure following a full thickness laceration of the dorsal tail skin. In further studies detailed below, it was discovered that the administration of DHEAS or DHEA to mice enhanced the re-epithelialization process following a scald burn on the dorsal trunk skin. In the final studies detailed below, the enhancement or acceleration of the re-epithelialization process is shown in a porcine model of partial thickness wound healing.

It has been discovered that the administration to a patient of a therapeutically effective amount of a DHEA derivative in a physiologically acceptable carrier as early as possible after an event that causes a physiological or mechanical disruption of an epithelial or endothelial surface, results in the acceleration or enhancement of re-epithelialization or re-endothelialization. It is preferred that the DHEA derivative be administered within four to twelve hours, more preferably four to six hours of the event. The acceleration of re-epithelialization or re-endothelialization results in earlier wound closure which is important to survival as previously noted. Although it is preferred to administer the DHEA derivative within four to six hours of the event, the DHEA derivative can be administered later and still enhance or accelerate re-epithelialization or re-endothelialization. The initial phase of healing of any wound requires the generation of a new surface (epithelial or endothelial) which serves as a barrier between sterile, vital tissue and the outside environment of the blood stream. The process of regrowth is the result of two other processes, migration and proliferation of the cells that form the epithelium or endothelium. The administration of a therapeutically effective amount of a DHEA derivative enhances or accelerates the process of regrowth to reduce the total time to wound closure.

Pharmaceutical compositions containing a DHEA derivative as the active ingredient in intimate admixture with a pharmaceutical carrier can be prepared according to conventional pharmaceutical compounding techniques. See, for example, *Remington's Pharmaceutical Sciences*, 17th Ed. (1985, Mack Publishing Co., Easton, Pa.). The carrier may take a wide variety of forms depending on the form of preparation desired for administration, e.g. intravenous or oral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). If desired, tablets may be sugar-coated or enteric-coated by standard techniques. The carrier may comprise sterile water, although other ingredients, for example, to aid solubility or for preservative purposes, may be included. Injectable solutions or suspensions may also be prepared, in which case appropriate liquid carriers, suspending agents and the like may be employed. It is preferred that the active ingredient be administered by intravenous injection.

The dose of the DHEA derivative is based on well known pharmaceutically acceptable principles to deliver a DHEAS equivalent dose of, e.g., 2–500 mg/kg, preferably 2–200 mg/kg, more preferably 5–200 mg/kg and most preferably 5–50 mg/kg. An especially preferred DHEAS equivalent dose is 5–40 mg/kg. Generally the dose of a DHEA derivative necessary to deliver this level of a DHEAS dose or a DHEAS equivalent dose is 1–1000 mg/kg, preferably 2–800 mg/kg, more preferably 2–500 mg/kg. The dose of DHEA derivative can be readily determined using conventional methods and will generally be in the range of the doses specified for DHEAS. For unprotected compounds, ie., those which can be sulfated by human sulfotransferases or sulfatases, it is preferred to administer an excess dose to insure that sufficient active agent is administered, especially if sulfatases are not active at the site of tissue injury. The patient is treated with a DHEA derivative as soon after the event requiring a re-epithelialization or a re-endothelialization of a tissue as possible until the tissue has been re-epithelialized or re-endothelialized. The treatment generally does not exceed 45 days, preferably 28 days and most preferably 7–14 days.

The present invention is described by reference to the following Examples, which are offered by way of illustration and are not intended to limit the invention in any manner. Standard techniques well known in the art or the techniques specifically described below were utilized.

EXAMPLE 1

DHEAS Treatment Enhances Wound Healing in Aged Mice In Vivo

WO 93/21711 demonstrates that IL-6 influences cellular responsiveness to PDGF and that DHEAS treatment restores T-cell responsiveness to PDGF. Since PDGF and various other growth factors are involved in wound healing, angiogenesis and other repair processes, this study was conducted to determine if DHEAS treatment could enhance wound healing.

Groups of mature adult mice (approximately 6 months of age, ▲), a control group of aged mice (greater than 2 years of age, ■), and another group of aged mice maintained on oral, supplemental DHEA-S (●) were compared for the relative rate of wound healing following a full thickness laceration of the dorsal tail skin. All mice were anesthetized and administered a precise laceration 2 cm from the base of the tail. The cut on each mouse was approximately 3 mm in length across the tail. Starting at 24 hours (day 1) and continuing daily for 18 days, mice were examined and given a numerical evaluation for the healing at the wound site. The wounds of both the mature adult and the DHEAS-treated aged mice showed steady healing of their wounds. These wounds were fully closed and scabbed within four days of injury. However, the untreated aged mice showed a much slower rate of healing, with wound closure and scabbing requiring about 14 days to develop. These results are shown in FIG. 1, where the following grading is used:

0=fresh laceration
1=fully open wound
2=closing from edges (halfway)
3=closing from edges (greater than halfway)
4=fully closed wound, swelling
5=fully scabbed wound, swelling
6=slight swelling
7=no swelling This example demonstrates that administration of DHEAS accelerates the rate of wound healing in aged animals.

EXAMPLE 2

Study of Burn Wound Re-epithelialization in the Mouse

Re-epithelialization of bum wounds was initially studied in a murine model of thermal injury. The dorsal trunk skin of anesthetized, six-week old Balb/c female mice was shaven and denuded with depilatory cream. Twenty-four hours later, each mouse was anesthetized and given an immersion, scald burn at 71° C., and a 5 second exposure. At four hours post-burn, mice were selected at random to receive another 12 mg/kg of DHEAS iv or placebo. Drug or placebo was given one time daily for six days. Under these conditions using juvenile mice, survival rates are 100%, and the depth of burn at 3 days post-injury with no therapeutic intervention is a deep second degree burn. Groups of two or three mice were euthanized from each of the treatment groups on days 3, 5 and 7 post-burn and the skin of the injured site was excised. The tissue was completely flattened, labeled and then immersed in 10% buffered formalin. After fixing for one week, the tissue is embedded in paraffm. Three complete strips, 5 mm in width, extending across the midline and including both burn margins were prepared from the excised, fixed tissue. Sections were cut at a thickness of 5 $\mu$m and stained with H and E for microscopic measurement of the linear distance of the re-epithelialized burn wound (% RE).

When administered to mice, partial thickness burn wounds are not protected with sterile dressings and can show a delay of 2–3 days in initiation of re-epithelialization. Among placebo-treated mice, re-epithelialization averaged 15% linear closure on day +3 (n=9), 35% closure on day 5 (n=9), and only 65% closure on day 7 (n=9). In contrast, DHEAS treatment accelerated the re-epithelialization process. We observed an average of 48% linear closure on day +3 (n=9), and 94% linear closure on day +5 (n=9). Since these wounds were considered to be closed on day 5, it was not surprising that the wounds excised from the thermally injured dorsal trunk skin of mice on day +7 were also fully closed. Similar results were obtained for DHEA.

Additional studies have determined that following thermal injury IGF-II and IGF-IL gene transcription is repressed in skin early after burn. However, therapeutic dosing of DHEAS following injury blocks burn-induced repression of the IGF genes in skin tissue. It is clear that re-epithelialization of partial thickness burn wounds can be studied in murine models. More importantly the result indicated that administration of DHEA/DHEAS intravenously reduced the time to complete closure of the wounds.

EXAMPLE 3

Study of Effects of DHEAS on Re-epithelialization in a Model of Partial Thickness Wound Closure in Pigs The objective of the present study was to determine the effects of two dose levels (4 and 12 mg/kg) of DHEAS in a porcine model of partial thickness wound healing induced by keratectomy. The methods would mimic the clinical situation in which epidermal tissue might be harvested by keratectomy from a donor graft site for application to a burn site. Efficacy of treatment with the test article was evaluated by measuring the extent of re-epithelialization (%RE), in comparison to treatment with the vehicle.

The time points chosen for evaluation of re-epithelialization after kerectomy wounds were based on those used in the literature (46, 47). Typically, this animal model of wound healing is used to evaluate topical, rather than systemic, treatment of the wounds. Multiple wounds are often collected from a single pig at different times by excisional biopsy under anesthesia (46, 48). Complete re-epithelialization of untreated (air-exposed) keratectomy wounds (% RE =100) in this model may take 6–7 days (46, 47), while coverage with an occlusive dressing may shorten the time required for complete re-epithelialization to 5 days (48). Wound healing (the plotted % RE) typically results in re-epithelialization that does not conform to a linear rate. Thus, $HT_{50}$ values are extrapolated from plots of % RE versus time (46, 47). Keratectomy wounds left untreated (control), covered with occlusive dressing, or treated with petrolatum, have been associated with $HT_{50}$ values of 4.3, 2.6 or ~5 days, respectively (46). This corresponds to RHR values of +40% and −16% for the occlusive dressing and petrolatum, respectively (46). At the Test Facility, the keratectomy model has previously yielded $HT_{50}$ values of 4.0 days for control (untreated) wounds and 3.1 days for wounds covered with an occlusive dressing.

A. Experimental Design

1. Overview

The study consisted of three groups of six animals per group. The animals in this study were instrumented with an indwelling catheter in the jugular vein for dose administration and received partial thickness keratectomy. Treatment consisted of intravenous administration of the vehicle or DHEAS at specified times. Blood was collected and processed for sera for assay. Subsequently, all animals were euthanized and the wounds were collected for evaluation of re-epithelialization.

2. Study Design

Text Table 1 summarizes the study design.

TABLE 1

| Group No. | No. of Animals | Wound Model | Substance | Treatment Dose (mg/kg) | Route | Time of Administration[1] | Euthanasia/ Tissue Collection |
|---|---|---|---|---|---|---|---|
| 1 (Control) | 6 | 4, 50 × 50 × 0.5 mm partial thickness blade wounds | Vehicle | DVE | IV | Once on Day 1 (Hours 4[2]) and Days 2, 3, 4, 5, 6, 7 | Two pigs on each of Days 4, 6 |
| 2 (Low Dose) | 6 | 4, 50 × 50 × 0.5 mm partial thickness blade wounds | DHEAS | 4 | IV | Once on Day 1 (Hours 4[2]) and Days 2, 3, 4, 5, 6, 7 | Two pigs on each of Days 4, 6 |
| 3 (High Dose) | 6 | 4, 50 × 50 × 0.5 mm partial thickness blade wounds | DHEAS | 12 | IV | Once on Day 1 (Hours 4[2]) and Days 2, 3, 4, 5, 6, 7 | Two pigs on each of Days 4, 6 |

DVE = Dose volume equivalent to high dose.
IV = Intravenous infusion over 10 minutes.
[1]Pigs were not dosed on their day of euthanasia.
[2]Hour 4 was considered to be four hours after the last wound was made.

3. Justifications

The study was designed to use a model of wound healing in pigs to evaluate the potential efficacy of a test article. The number of animals used in this study was considered the minimum number acceptable for evaluation of the results. This product required evaluation of its performance using an in vivo model, since its anticipated use will be in humans. Pigs are an accepted model for wound healing studies because of the similarity of their skin to human skin. The treatment regimen stimulates the anticipated administration in humans.

B. Materials And Methods

1. Animals

Receipt: Twenty female Yorkshire pigs were received on Dec. 27, 1995 from Earl M. Parsons and Sons, Inc., Hadley, Mass. Upon receipt, the pigs were examined for clinical signs of disease or injury, and weighed from 19.2 to 24.3 kg.

Quarantine: The pigs were quarantined for seven days. During this period, the pigs were housed in pens and acclimated to the environmental conditions used for the study. The animals were released from quarantine on Jan. 02, 1996 following a visual inspection to evaluate their health status by Marek Piechowiak.

Acclimation: During quarantine, all study animals were acclimated to wearing a protective aluminum jacket prior to the surgical procedure and were handled daily so that they became acclimated to close human contact.

Identification/Randomization: Each animal was identified with a unique number that was indicated with a ear tag. Color-coded cage labels identified each cage with study number, group number, sex, species, individual animal identification number and Study Director. The animals were randomized into three groups by computer-generated random number selection.

2. Test Article

Receipt: On Dec. 19, 1995, 90 vials, each containing 200 mg of the test article, DHEAS-IV, were received from Pharmaco-LSR, Austin, Tex. 78704. The test article and control articles were described as white, crystalline powders, and were stored at 22±5° C. by the Test Facility. The diluent, Sterile Water for Injection (SWI), USP, supplied by the Test Facility, was described as a clear liquid, and was stored at 22±5° C. by the Test Facility.

Formulation: Intravenous dose formulations were prepared daily at a concentration of 10 mg/mL using sterile equipment and technique according to the following procedures. A supply of Sterile Water for Injection (SWI), sufficient for reconstitution of the desired number of vials, was warmed to 34–40° C. in a water bath. Under a laminar flow hood, 20 mL of SWI were aseptically transferred to each vial of vehicle or test article needed. The contents of each reconstituted vial were mixed by gently shaking. Formulated test materials were stored at ambient temperature prior to use, and were used within two hours of preparation.

3. Surgical Procedures—Preoperative

Anesthesia: The pigs were initially anesthetized with a mixture of ketamine HCl (25 mg/kg), atropine (0.04 mg/kg), butorphanol (0.55 mg/kg) and xylazine (2 mg/kg), administered intramuscularly. The pigs were intubated and maintained in anesthesia with isoflurane inhalant anesthetic, delivered through a volume-regulated respirator. A percutaneous catheter was placed in a peripheral vein for intravascular access, if necessary. Drugs for appropriate anesthetic management were available for administration if indicated.

Antibiotic Administration: Procaine/benzathine penicillin G (1 mL/4.5 kg, IM) was administered prior to surgery. The dose, route, time and site of administration were recorded.

Surgical Preparation: For each animal the torso, back and sites of jugular vein catheterization and exteriorization of the jugular catheters were clipped of all hair. These sites were cleaned with three alternating scrubs of povidone-iodine scrub solution and 70% isopropyl alcohol, with a final application of povidone-iodine solution that was allowed to dry. The operative sites were appropriately draped for aseptic surgery.

Surgical Procedures: Details of the surgical techniques were documented in a Surgical Techniques Memorandum (Appendix A).

Wound Creation: Keratectomy: Two square wounds measuring approximately 50×50 c 0.5 mm were made on each side of the animal (four blade wounds per animal) in the dorsal paravertebral and thoracic area skin with a nitrogen-powered dermatome.

Catheterization: A jugular vein was surgically isolated and catheterized. The catheter was tunneled subcutaneously and exteriorized on the pig's dorsal midline. After placement of the catheter, the incision was closed. The catheter and wounds were protected by an aluminum jacket placed on the pig.

4. Surgical Procedures—Postoperative

Postoperative Analgesia: The pigs were given buprenorphine (0.03 mg/kg, IV) and acetylpromazine (0.75 mg/kg, IV) prior to extubation for post-operative analgesia and to facilitate recovery from anesthesia, respectively. Buprenorphine was then administered for two additional days. If deemed appropriate by the Study Director or Test Facility Veterinarian, additional analgesic agents were administered. The dose, route and site of administration for all analgesics were documented in the study file.

Incision Sites: The surgical incisions were observed twice daily for signs of infection, inflammation and general integrity.

Catheter Maintenance: The jugular catheter was filled and "locked" as appropriate. All procedures adhered to aseptic technique. Additional procedures were performed as necessary to maintain catheters.

Dressing Maintenance: A protective aluminum jacket was placed on each animal to prevent disruption of the bandages. The aluminum jacket and the bandages were checked twice daily and replaced or adjusted as necessary. The Tegaderm™ was replaced daily or as necessary.

5. Treatment

Treatment with the vehicle or DHEAS was administered over 10 minutes using a clinical grade infusion pump by intravenous infusion (via an indwelling catheter in the jugular vein) at the times specified in Table 1. Dose volumes were calculated based on the most recent body weight and were rounded to the nearest 0.1 mL. Administration of the test materials was documented for each animal; volume, time and site were recorded.

6. Wound Biopsy

All animals were anesthetized and all wounds were excised and pinned in a flat position and immersed in 10% neutral buffered formalin for fixation. Approximately 24 hours later, the biopsies were unpinned and transferred to appropriately-labeled containers of 10% neutral buffered formalin. After fixation, a 5 mm strip from the center of each wound was trimmed and processed for histopathology.

Special Histology: For all animals, biopsied wounds were sectioned in toto, and mounted on large microscope slides.

7. Pathology

Euthanasia: Euthanasia (tranquilization with ketamine and xylazine, if necessary, if necessary, followed by anesthesia and euthanasia with sodium pentobarbital, 25 mg/kg, IV, and if necessary, exsanguination) was performed in accordance with accepted American Veterinary Medical Association guidelines [Report of the American Veterinary Medical Association (AVMA) Panel on Euthanasia, Journal of the American Veterinary Medical Association, 202:229–249 (1993)].

8. Data Analysis

Evaluation of Wound Healing: Keratectomy wounds were evaluated separately. The histopathology slides for each wound were reviewed and the total linear distance of each wound and the linear distance covered by migrating epithelial cells were measured. The following calculations were performed:

% re-epithelialization for each keratectomy $$\% RE_K = \frac{\text{linear distance re-epithelialized}}{\text{linear distance total wound}} \times 100$$

% re-epithelialization for each treatment at each time point:

$$\% RE_{KT} = \frac{\sum \% RE_K}{\text{number of wounds}}$$

Figure 2:
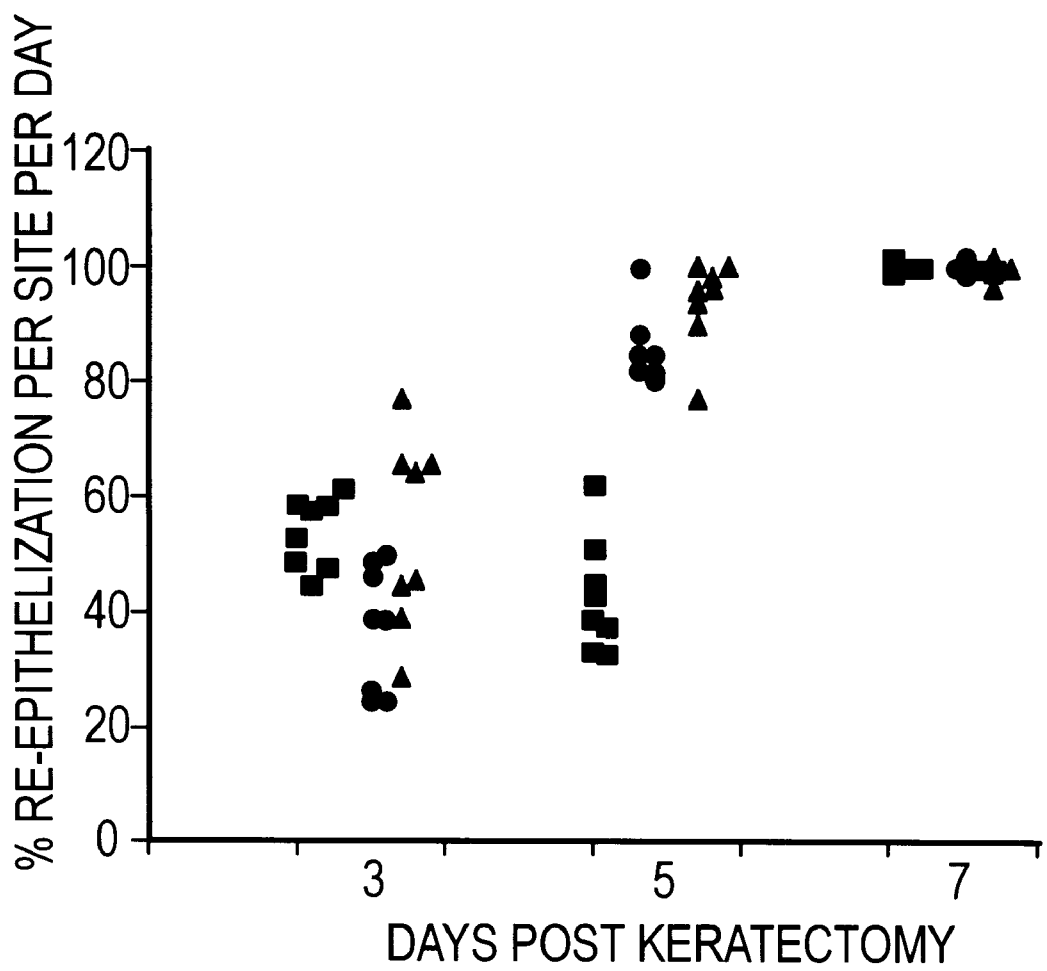
FIG. 2 shows the effect of DHEAS on closure of keratectomy sites in pigs as expressed in % re-epithelialization per site per day.
Figure 3:
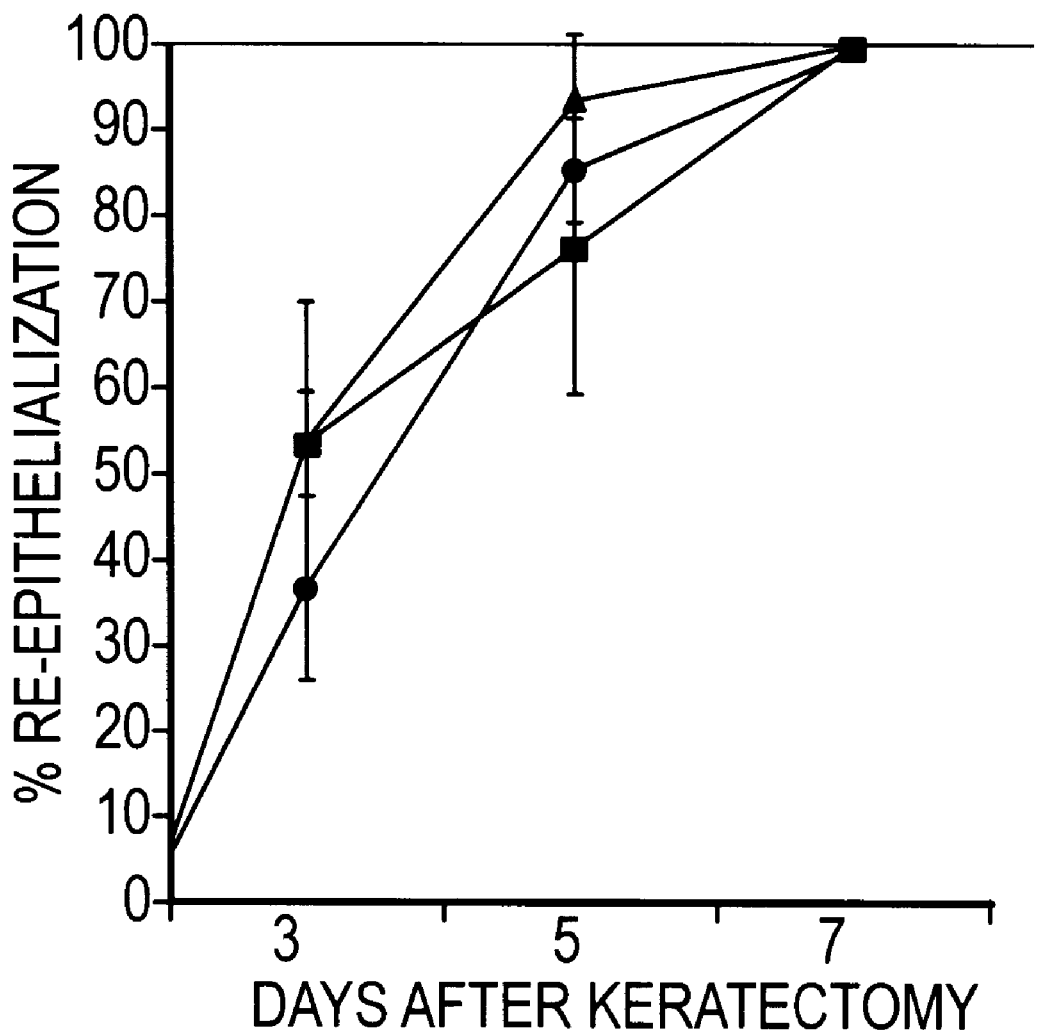
FIG. 3 shows a graphical illustration of the results of keratectomy-induced wound closure. The results in FIG. 3 are as for FIG. 2.

Wound healing data are presented in Table 2. The effect of DHEAS on closure of keratectomy sites in pigs is shown in FIGS. 2 and 3. These figures show the results for the control (vehicle, ■), 4 mg/kg dose of DHEAS (●) and 12 mg/kg dose of DHEAS (▲).

TABLE 2

Effect of Placebo vs. 4 mg/kg or 12 mg/kg DHEAS on Re-Epithelialization of Keratectomy Wounds in Pig Model

| Treatment | Placebo Treated (12 mg/kg/day × 7 Days) | Low Dose DHEAS (4 mg/kg/day × 7 Days) | High Dose DHEAS (12 mg/kg/day × 7 Days) |
|---|---|---|---|
| % RE d0 (mean SD) | 1.5 ± 1.5 | 1.5 ± 1.5 | 1.5 ± 1.5 |
| % RE d.3 (mean SD) | 53.54 ± 6.07 | 36.9 ± 10.95 | 53.61 ± 16.64 |
| % RE d.5 (mean SD) | 76.52 ± 16.93 | 85.65 ± 6.18 | 93.84 ± 7.67 |
| % RE d.7 (mean SD) | 100 ± 0 | 100 ± 0 | 99.59 ± 1.163 |
| r = | 0.9760 | 0.9909 | 0.9674 |
| 95% CV | .09445–0.9897 | 0.9786–0.9961 | 0.9250–0.9860 |
| n = | 24 | 24 | 24 |
| time to closure (days) | 6.9 | 5.8 | 5.3 (<0.05 vs. placebo) |

9. Results

All animals were euthanized according to a randomization schedule on days 3, 5 or 7. Both keratectomy and burn wounds were excised and prepared for histologic evaluation of re-epithelialization. Analysis of the linear length of each keratectomy and the linear length of re-epithelialization of each was used to calculate the percentage of the wound re-epithelialized at each time interval. Linear regression analysis was then employed to derive the mean time to 100% re-epithelialization for wounds in placebo vs. test article treatment groups. The results of this study are given in Table 2. Closure in the placebo-treated group was linear, with a mean time to closure of 6.9 days. For the 12 mg/kg dose of DHEAS, wounds were 94% closed at five days and the regression analysis calculated a mean time to closure of 5.3 days (p<0.05 vs. placebo). The wounds of pigs in the 4 mg/kg dose of DHEAS were 86% closed by day five, which indicated a mean time to complete closure of 5.8 days.

The conclusion drawn from this experiment is that DHEAS IV had a significant biological effect on reducing the mean time to closure of keratectomy wounds in a pig model. The predicted mean time for closure for the placebo was not different from the histologic measurements, around seven days to completion. Administration of DHEAS clearly shortened the time to complete closure of keratectomy wounds by approximately two days.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES (1) Clark, R. A. F. and Henson, P. M. (1988). *The Molecular and Cellular Biology of Wound Repair*. New York, Plenum Press.

(2) Arey, L. B. (1936). Wound healing. *Physiol. Rev.* 16:327–406.

(3) Marks, R. and Nishikawa, T. (1973). Active epidermal movement in human skin in vitro. *Brit. J. Dermatol.* 86:481–490.

(4) Kuwabara, T. et al.(1976). Sliding of the epithelium in experimental corneal wounds. *Invest. Ophthalmol.* 15:4–14.

(5) Pang, S. C. et al. (1978). Epidermal migration during the healing of suction blisters in rat skin: A scanning and transmission electron microscopic study. *Am. J. Anat.* 153:177–191.

(6) Winter, G. D. (1972). Epidermal regeneration studied in the domestic pig. In *Epidermal Wound Healing*, Mailbach, H. I. and Rovee, D. T. (eds.), Year Book, Chicago, pp 71–112.

(7) DiPasquale, A. (1975). Locomotion of epithelial cells. *Exp. Cell. Res.* 95:425–439.

(8) Dunlap, M. K. and Donaldson, D. J. (1978). Inability of colchicine to inhibit newt epidermal cell migration or prevent concanavalin A—mediated inhibition of migration studies. *Exp. Cell. Res.* 116:15–19.

(9) Gipson, I. K. et al. (1982). Effects of cytochalasins B and D and colchicine on migration of corneal epithelium. *Invest. Ophthalmol. Vis. Sci.* 22:633–642.

(10) Gillman, T. et al. (1963). Reactions of healing wounds and granulation tissue in man to autothiersch, autodermal and homodermal grafts. *Brit. J. Plast. Surg* 6:153–223.

(11) Hinshaw, J. R. and Miller, E. R. (1965). Histology of healing split-thickness, full thickness autogenous skin grafts and donor sites. *Arch. Surg.* 91:658–670.

(12) Chong, ASF, et al. (1987). Expression of cytokeratins in fibroblasts in induced by reconstituted basement membrane. *J Cell. Biol.* 105:49a.

(13) Krawczyk, W. S. (1971). A pattern of epidermal cell migration during wound healing. *J. Cell. Biol.* 49:247–263.

(14) Mansbridge, J. N. and Knapp, A. M. (1987). Changes in keratinocyte maturation during wound healing. *J. Invest. Dermatol.* 89:253–263.

(15) Odland, G. and Ross, R. (1968). Human wound repair. I. Epidermal regeneration. *J. Cell. Biol.* 39:139–151.

(16) Fejerskov, O.(1972). Excision wounds in palatal epithelium in guinea pigs. *Scan. J. Dent. Res.* 80:139–154.

(17) Gibbins, J. R. (1968). Migration of stratified squamous epithelium in vivo. *Am. J. Pathol.* 53:929–941.

(18) Anderson, L. and Fejerskov, O. (1974). Ultrastructure of initial epithelial cell migration in palatal wounds of guinea pigs. *J. Ultrastructure Res.* 48:313–324.

(19) Gabbiani, G. and Ryan, G. B. (1974). Development of a contractile apparatus in epithelial cells during epidermal and liver regeneration. *J. Submier. Cytol.* 6:143–157.

(20) Betchaku, T. and Trinkaus, J. P. (1978). Contact relations, surface activity and cortical microfilaments of marginal cells of the enveloping layer and of the yolk synetail and yolk cytoplasmic layers of Fundulus before and during epiboly. *J. Exp. Zool.* 206:381–426.

(21) Takashima, A. and Grinnell, F. (1984). Human keratinocyte adhesion and phagocytosis promoted by fibronectin. *J. Invest. Dermatol.* 83:352–358.

(22) Vaughan, R. B. and Trinkaus, J. P. (1966). Movements of epithelial cell sheets in vitro. *J. Cell. Sci.* 1:407–413.

(23) Radice, G. (1980). The spreading of epithelial cells during wound closure in Xenopus larvae. *Develop. Biol.* 76:26–46.

(24) Bellairs, R. (1963). Differentiation of the yolk sac of the chick studied by electron microscopy. *J. Embryol. Exp. Morphol.* 11:201–225.

(25) Buck, R. C. (1979). Cell migration in repair of mouse corneal epithelium. *Invest. Opthalmol. Vis. Sci.* 18:767–784.

(26) Winter, G. D. (1964). Movement of epidermal cells over the wound surface. *Dev. Biol. Skin.* 5:113–127.

(27) Ortonne, J. P. et al. (1981). Immunomorphological and ultrastructural aspects of keratinocyte migration in epidermal wound healing. *Virchow. Arch. A* 392:217–230.

(28) Beerens, E. G. T. et al. (1975). Rapid regeneration of the dermal-epidermal junction after partial separation by vacuum. An electron microscopic study. *J. Invest. Dermatol.* 65:513–521.

(29) Sciubba, J. J. (1977). Regeneration of the basal lamina complex during epithelial wound healing. *J. Periodont. Res.* 12:204–217.

(30) Gibbins, J. R. 91978). Fpithelial migration in organ culture. A morphological and time lapse cinematographic analysis of migrating stratified squamous epithelium. *Pathology* 10:207–218.

(31) Stenn, K. S and DePalma, L. (1988) Re-epithelialization. In *The Molecular and Cellular Biology of Wound Repair*, Clark, R. A. F. and Henson, P. M. (eds), Plenum Press, New York, pp 321–335.

(32) De Peretti, E. et al. (1978). *J. Clin. Endocrinol. Metab.* 47:572.

(33) Swartz, A.G. et al. (1981). *Nutr. Cancer* 3:46.

(34) Yen, T. T. et al. (1977). *Lipids* 12:409.

(35) Coleman, D. C. (1982). *Diabetes* 31:830 (1982).

(36) Flood, J. F. (1988). *Brain Res.* 447:269

(37) Daynes, R. A. et al. (1990). *Eur. J. Immunol.* 19:2319.

(38) Araneo, B. A. et al. (1993). *Arch. Surg.* 128:318–325.

(39) Eich, D. M. et al. (1992). U.S. Pat. No. 5,110,810.

(40) Eich, D. M. et al. (1992). U.S. Pat. No. 5,162,198.

(41) Nestler, J. E. et al. (1990). U.S. Pat. No. 4,920,115.

(42) Kent, S. (1982). *Geriatrics* 37:157–159.

(43) Daynes, R. A et al. (1994). WO 94/20111.

(44) Daynes R. A. et al. Ser. No. 08/480,744, filed Jun. 7, 1995.

(45) Araneo, B. A. et al. Ser. No. 08/580,716, filed Dec. 29, 1995.

(46) Eaglstein, W. H. and Mertz, P. M. (1978). New method for assessing epidermal wound healing: The effects of triamcinolone acetonide and polyethylene film occlusion. *J. Invest. Dermatol.* 71:382–384.

(47) Winter, G. D. (1962). Formation of the scab and the rate of epithelialization of superficial wounds in the skin of the young domestic pig. *Nature* 193:293–294.

(48) Davis, S. C. et al. (1990). Second degree burn healing: The effect of occlusive dressings and a cream. *J. Surg. Res.* 48:245–248.

What is claimed is:

1. A method for accelerating re-epithelialization or re-endothelialization which comprises administering to a subject in need of re-epithelialization or re-endothelialization an effective amount of a dehydroepiandrosterone (DHEA) derivative in a pharmaceutically acceptable vehicle.

2. The method of claim 1, wherein said DHEA derivative has the general formula

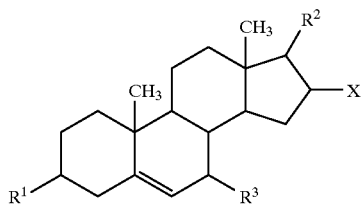

wherein
   X is H or halogen;
   $R^1$, $R^2$ and $R^3$ are independently =O, —OH, —SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —$OSO_2R^5$ or —$OPOR^5R^6$;
   $R^5$ and $R^6$ are independently —OH, pharmaceutically acceptable esters or pharmaceutically acceptable ethers; and
   pharmaceutically acceptable salts.

3. The method of claim 2, wherein said DHEA derivative is administered intravenously.

4. The method of claim 1, wherein said DHEA derivative is dehydroepiandrosterone sulfate.

5. The method of claim 3, wherein said DHEA derivative is administered intravenously.

6. The method of claim 1, wherein said DHEA derivative is dehydroepiandrosterone.

7. The method of claim 4, wherein said DHEA derivative is administered intravenously.

8. The method of claim 1, wherein said DHEA derivative is administered intravenously.

9. The method of claim 1, wherein the compound is administered in the amount of 1–1000 mg/kg.

10. The method of claim 1, wherein the compound is administered in the amount of 2–500 mg/kg.

11. The method of claim 1, wherein the compound is administered in the amount of 2–200 mg/kg.

12. The method of claim 1, wherein the compound is administered in single or multiple doses.

13. The method of claim 1, wherein the compound is administered in a DHEAS equivalent amount of 2–500 mg/kg.

14. The method of claim 1, wherein the compound is administered in a DHEAS equivalent amount of 2–200 mg/kg.

15. The method of claim 1, wherein the compound is administered in a DHEAS equivalent amount of 5–200 mg/kg.

16. The method of claim 1, wherein the compound is administered in a DHEAS equivalent amount of 5–50 mg/kg.

17. The method of claim 1, wherein the compound is administered in a DHEAS equivalent amount of 5–40 mg/kg.

18. The method of claim 1, wherein the compound is administered within four to twelve hours of an event that causes a physiological or mechanical disruption of an epithelial or endothelial surface.

19. The method of claim 1, wherein the compound is administered within four to six hours of an event that causes a physiological or mechanical disruption of an epithelial or endothelial surface.

* * * * *

UNITED STATES PATENT AND TRADEMARK OFFICE
CERTIFICATE OF CORRECTION

PATENT NO. : 5,929,060
DATED : July 27, 1999
INVENTOR(S) : Araneo

Page 1 of 1

It is certified that error appears in the above-identified patent and that said Letters Patent is hereby corrected as shown below:

Column 7,
Line 22 and 23, "ethers or thioethers" should be -- esters or thioesters --.
Line 45, "bum" should be -- burn --.

Column 10,
Line 10, "IGF-11 and IGF-IL" should be -- IGF-I and IGF-II --.

Column 16,
Line 33, "91978)" should be -- (1978) --; and "Fpithelial" should be -- Epithelial --.

Column 17,
Line 38, "3" should be -- 4 --.

Column 18,
Line 1, "4" should be -- 6 --.

Signed and Sealed this

Twenty-third Day of October, 2001

Attest:

*Nicholas P. Godici*

NICHOLAS P. GODICI
*Attesting Officer*  *Acting Director of the United States Patent and Trademark Office*

UNITED STATES PATENT AND TRADEMARK OFFICE
CERTIFICATE OF CORRECTION

PATENT NO.      : 5,929,060
DATED           : July 27, 1999
INVENTOR(S)     : Araneo It is certified that error appears in the above-identified patent and that said Letters Patent is hereby corrected as shown below:

<u>Column 1,</u>
Line 21, please insert the following paragraph before the section beginning with "BACKGROUND OF THE INVENTION":

-- STATEMENT REGARDING FEDERALLY SPONSORED RESEARCH OR DEVELOPMENT

This invention was made with Government support under Grant No. GM46899, awarded by the National Institututes of Health, Bethesda, Maryland, and under Grant No. 0014-92-J-1612, awarded by the Department of the Navy. The United States Government has certain rights in the invention. --

Signed and Sealed this

Sixth Day of January, 2004

JAMES E. ROGAN
*Director of the United States Patent and Trademark Office*